United States Patent
Morris et al.

(10) Patent No.: US 10,652,808 B2
(45) Date of Patent: May 12, 2020

(54) RADIO NETWORK COMMUNICATION MODES IN PHYSIOLOGICAL STATUS MONITORING

(71) Applicant: COVIDIEN LP, Mansfield, MA (US)

(72) Inventors: Benjamin David Morris, Annapolis, MD (US); Istvan Roland Fellner, Auckland (NZ); Jeremy Jun Wong, Tokyo (JP)

(73) Assignee: Covidien LLP, Mansfield, MA (US)

( * ) Notice: Subject to any disclaimer, the term of this patent is extended or adjusted under 35 U.S.C. 154(b) by 89 days.

(21) Appl. No.: 15/239,400

(22) Filed: Aug. 17, 2016

(65) Prior Publication Data

US 2017/0055205 A1    Feb. 23, 2017

Related U.S. Application Data

(60) Provisional application No. 62/206,626, filed on Aug. 18, 2015.

(51) Int. Cl.

| | |
|---|---|
| *H04W 48/18* | (2009.01) |
| *G06F 19/00* | (2018.01) |
| *H04L 29/08* | (2006.01) |
| *H04W 48/02* | (2009.01) |
| *A61B 5/00* | (2006.01) |
| *H04W 84/18* | (2009.01) |
| *A61B 5/0205* | (2006.01) |

(52) U.S. Cl.
CPC ........... *H04W 48/18* (2013.01); *A61B 5/0015* (2013.01); *G06F 19/3418* (2013.01); *H04L 67/12* (2013.01); *H04W 48/02* (2013.01); *A61B 5/0205* (2013.01); *A61B 2503/10* (2013.01); *H04W 84/18* (2013.01)

(58) Field of Classification Search
CPC ..... H04W 48/02; H04W 48/18; H04W 84/18; H04L 67/12; G06F 19/3418; A61B 2503/10; A61B 5/0015; A61B 5/0205
See application file for complete search history.

(56) References Cited

U.S. PATENT DOCUMENTS

| | | | |
|---|---|---|---|
| 2005/0197680 A1* | 9/2005 | DelMain | A61B 5/0031 607/60 |
| 2007/0150565 A1* | 6/2007 | Ayyagari | H04L 67/12 709/223 |
| 2007/0253021 A1* | 11/2007 | Mehta | A61B 5/0002 358/1.15 |
| 2008/0253327 A1* | 10/2008 | Kohvakka | H04W 16/14 370/330 |
| 2009/0247094 A1* | 10/2009 | Sakoda | H04W 16/14 455/78 |

(Continued)

*Primary Examiner* — Erica Navar
(74) *Attorney, Agent, or Firm* — Holland & Hart LLP

(57) ABSTRACT

Methods, apparatuses and systems are described for managing communication modes on a network used for physiological status monitoring. The methods may include receiving indications that a network had been selected and that a communication or operation mode for the network had been selected. The communication or operation mode may be based at least in part on a number of remote physiological monitoring devices that are to be allowed to communicate on the radio access network. A beacon may be transmitted to indicate one or more transmission parameters associated with the selected communication or operation mode.

18 Claims, 10 Drawing Sheets

(56) References Cited

U.S. PATENT DOCUMENTS

| | | | |
|---|---|---|---|
| 2011/0149759 A1* | 6/2011 | Jollota | A61B 5/0024 370/252 |
| 2012/0054353 A1* | 3/2012 | Jung | H04W 88/04 709/227 |
| 2015/0078382 A1* | 3/2015 | Morosawa | H04L 45/54 370/392 |

* cited by examiner

RADIO NETWORK COMMUNICATION MODES IN PHYSIOLOGICAL STATUS MONITORING

CROSS REFERENCE

The present application for patent claims priority to U.S. Provisional Patent Application No. 62/206,626 by Morris et al., entitled "Radio Network Communication Modes in Physiological Status Monitoring," filed Aug. 18, 2015, assigned to the assignee hereof.

BACKGROUND

The present disclosure relates generally to communication using physiological and activity monitoring systems, and more particularly to the use of multiple transmission modes in a mesh network for communications using physiological and activity monitoring systems.

Use of mobile personal monitoring devices in sports and physical activity applications is well known, but many of these activity monitors may be limited in their functionality. Some limitations may occur with respect to quantifying and contextualizing monitored physiological data. Other limitations may relate more to the number of users who may be simultaneously monitored. For example, in certain applications or networks, the number of users to be monitored may exceed a maximum number of users supported by the network. In one example, a trainer or coach may desire to monitor the activities of individual team members during a training session. If, however, the number of team members to be monitored exceeds the number supported by the network, the trainer or coach may be confronted with less desirable options such as only monitoring a portion of the team at any given time, swapping personal monitoring devices between players, or adding another network or expanding the existing network supporting communications with the personal monitoring devices. Similarly, in a hospital environment, a nurse or doctor having more patients with personal monitoring devices than can be supported by a communications network may likewise be forced to reduce the number of patients being remotely monitored, thus increasing the number of physical monitoring visits that must be performed, or expand the supporting network.

Accordingly, improvements to allow differing numbers of users and/or devices to communicate on a network for physiological and activity monitoring systems may be beneficial.

SUMMARY

A mesh network may be used to provide communication for physiological and activity monitoring systems. For example, a mesh network may be used to provide communications within a training facility or within a hospital. The mesh network may include options to accommodate different numbers of users and/or devices. The mesh network may include various operating modes, with each mode being based on a different maximum number of devices to be used on the network. When the mesh network is established or updated, a user may select from the available modes. The network may then operate under communication protocols appropriate for the selected mode. For example, a twenty-subject mode may include a one-second update rate. A fifty-subject mode may include a two and a half-second update rate. A one-hundred-subject mode may include a five-second update rate. Other communication parameters and protocols may be adjusted for each mode.

In operation, a beacon may be transmitted by the network at the beginning of each update period. Devices on the network may reply to the beacon at the appropriate interval based at least in part on a received short address. In this way, the network may be dynamically updated to operate in different modes. User devices may function in response to the updates, thus allowing the network to be centrally updated. Additionally, a network identification may be added to the beacon to distinguish the beacon from other beacons sent in overlapping networks. In one example, the network may also prevent deployment of more than a maximum number of subjects permitted based upon the selected mode. In other aspects, additional modes may be utilized having smaller maximum numbers of devices to allow for faster refresh rates.

The present disclosure provides a method of wireless communication in a physiological status monitoring system. In some embodiments, the method may include: receiving a network indication that a radio access network has been selected; receiving a mode indication that an operation mode of the radio access network has been selected, the operation mode based at least in part on a number of remote physiological monitoring devices that are to be allowed to communicate on the radio access network; and transmitting a beacon indicating to the remote physiological monitoring devices one or more transmission parameters associated with the operation mode.

In some embodiments, the method may further include receiving transmissions from one or more of the remote physiological monitoring devices in accordance with the one or more transmission parameters.

In some embodiments, the method may further include selecting the beacon for transmission from among a plurality of preconfigured beacons corresponding to different operating modes.

In some embodiments, the method may further include receiving transmissions from one or more of the remote physiological monitoring devices at varying update rates, the update rates varying based on the operation mode.

In some embodiments, the method may further include operating in one of a low capacity operation mode, a medium capacity operation mode, or a high capacity operation mode. In some embodiments, the one or more transmission parameters may indicate that the remote physiological monitoring devices are to provide updated data at a first update rate during operation in the low capacity operation mode, at a second update rate during operation in the medium capacity operation mode, and at a third update rate during operation in the high capacity operation mode.

In some embodiments, the first update rate may have an update frequency that is faster than an update frequency of the second update rate. In some embodiment, the second update rate may have an update frequency that is faster than an update frequency of the third update rate.

In some embodiments, transmitting the beacon indicating to the remote physiological monitoring devices one or more transmission parameters associated with the operation mode may include including one or more transmission parameters an indication that the remote physiological monitoring devices are to provide updated data during transmission slots whose lengths vary in accordance with the operating mode.

In some embodiments, transmitting the beacon indicating to the remote physiological monitoring devices one or more transmission parameters associated with the operation mode may include including the network indicator in the beacon.

In some embodiments, the method may further include prohibiting an addition of a remote physiological monitoring device to the radio access network when a total number of remote physiological monitoring devices registered to the radio access network is equal to the number of remote physiological monitoring devices that are to be allowed to communicate on the radio access network for the operation mode.

In some embodiments, the method may further include receiving transmissions from one or more of the remote physiological monitoring devices. In some embodiments, the transmissions may include a short address of a transmitting remote physiological monitoring device. In some embodiments, a range of available short addresses may vary in accordance with the operation mode.

The present disclosure may also relate to a physiological status monitoring device. In some embodiments, the physiological status monitoring device may include a transceiver configured to transmit and receive communications from one or more remote physiological monitoring devices and a processor. In some embodiments, the processor may be configured to execute instructions to: receive a network indication that a radio access network has been selected; receive a mode indication that an operation mode of the radio access network has been selected, the operation mode based at least in part on a number of remote physiological monitoring devices that are to be allowed to communicate on the radio access network; and transmit a beacon indicating to the remote physiological monitoring devices one or more transmission parameters associated with the operation mode.

The present disclosure may also relate to a non-transitory computer-readable medium storing computer executable code. In some embodiments, the code may be executable by a processor to: receive a network indication that a radio access network has been selected; receive a mode indication that an operation mode of the radio access network has been selected, the operation mode based at least in part on a number of remote physiological monitoring devices that are to be allowed to communicate on the radio access network; and transmit a beacon indicating to the remote physiological monitoring devices one or more transmission parameters associated with the operation mode.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

A mesh network may be used to provide communication for physiological and activity monitoring systems. For example, communications on the mesh network may be in accordance with the IEEE 802.15.4 standard, using, for example, time division multiplexing (TDM). Thus, for example, communication on the mesh network may be divided into discrete time intervals, with each time interval allowing for communications from or to individual devices. Individual devices may each be assigned a time slot during which communications specific to the device may be made. Thus, the number of time slots, the duration of each time slot, and the duration of the total update period may be varied based on a maximum number of devices expected to use the network.

Therefore, the mesh network may include options to accommodate different numbers of users and/or devices. The mesh network may include various operating modes, with each mode being based on a different maximum number of devices to be used on the network. When the mesh network is established or updated, a user may select from the available modes. The network may then operate under communication protocols appropriate for the selected mode. For example, a twenty-subject mode may include a one-second update rate. A fifty-subject mode may include a two and a half-second update rate. A one-hundred-subject mode may include a five-second update rate. Other communication parameters and protocols may be adjusted for each mode.

In operation, a beacon may be transmitted by the network at the beginning of each update period. Devices on the network may reply to the beacon at the appropriate interval based at least in part on a received short address. In this way, the network may be dynamically updated to operate in different modes. User devices may function in response to the updates, thus allowing the network to be centrally updated. Additionally, a network identification may be added to the beacon to distinguish the beacon from other beacons sent in overlapping networks. In one example, the network may also prevent deployment of more than a maximum number of subjects permitted based upon the selected mode. In other aspects, additional modes may be utilized having smaller maximum numbers of devices to allow for faster refresh rates.

Figure 1:
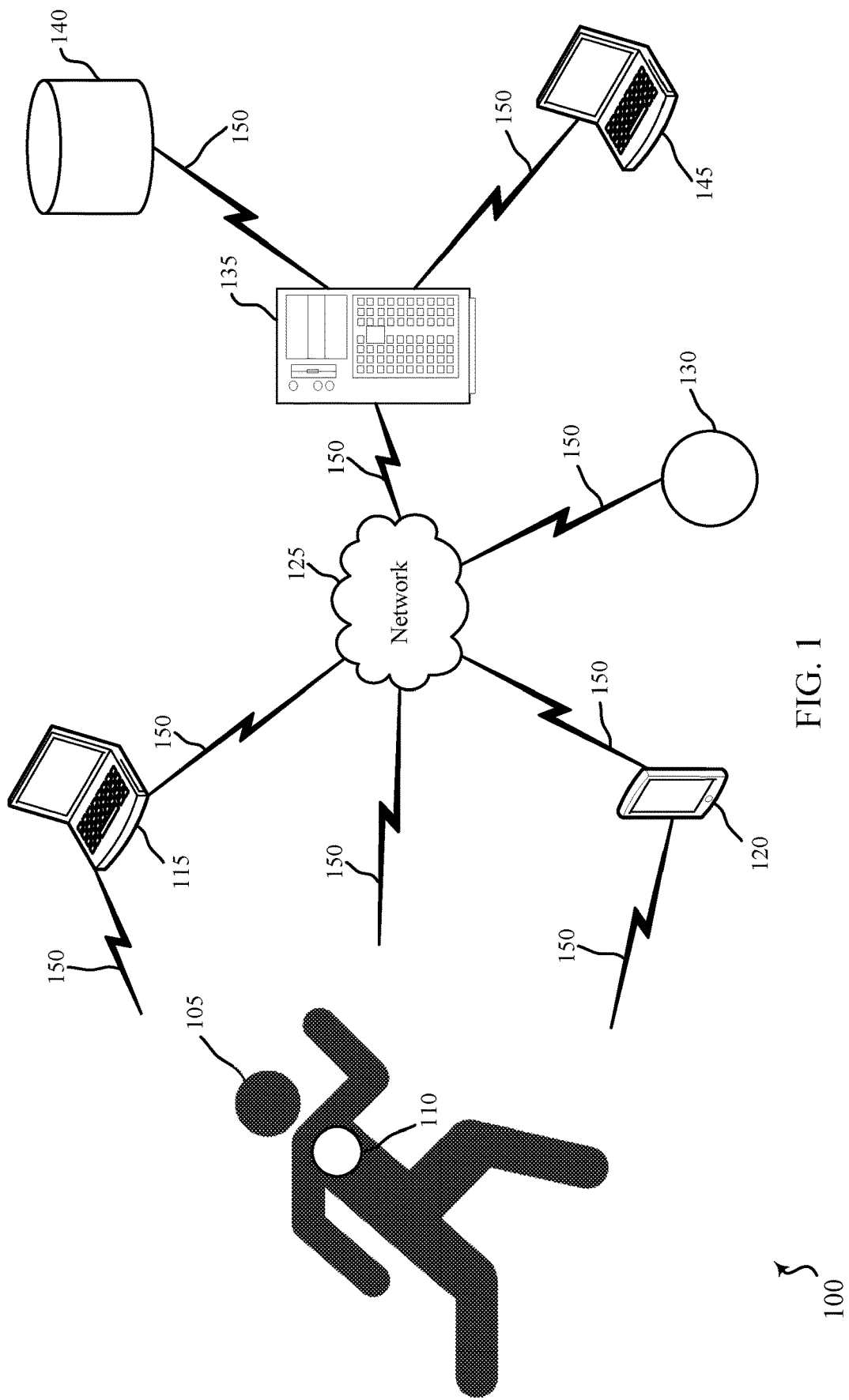
FIG. 1 is a block diagram of an example of a physiological and activity monitoring system, in accordance with various embodiments.

Referring first to FIG. 1, a diagram illustrates an example of a physiological and activity parameter monitoring system 100. The system 100 includes user 105, wearing one or more sensor units 110. The user 105 may be an athlete in some examples, may be a patient in other examples, or in some instances may be a layperson interested in simply monitoring various aspects of his or her daily activities. The sensor units 110 transmit signals via wireless communication links 150. The transmitted signals may be transmitted to local computing devices 115, 120. Local computing device 115 may be a local caregiver's station, for example. Local computing device 120 may be a mobile device, for example. The local computing devices 115, 120 may be in communication with a server 135 via network 125. The sensor units 110 may also communicate directly with the server 135 via the network 125. Additional, third-party sensors 130 may also communicate directly with the server 135 via the network 125. The server 135 may be in further communication with a remote computing device 145, thus allowing a caregiver to remotely monitor the user 105. The server 135 may also be in communication with various remote databases 140 where the collected data may be stored.

The sensor units 110 are described in greater detail below. Each sensor unit 110 is capable of sensing multiple physiological and activity parameters. Thus, the sensor units 110 may each include multiple sensors such as heart rate and ECG sensors, respiratory rate sensors, and accelerometers. For example, a first sensor in a sensor unit 110 may be an oxygen saturation monitor or a glucose level monitor operable to detect a user's blood oxygen or sugar levels. A second sensor within a sensor unit 110 may be operable to detect a second physiological parameter. For example, the second sensor may be a heart rate monitor, an electrocardiogram (ECG) sensing module, a breathing rate sensing module, and/or any other suitable module for monitoring any suitable physiological parameter. Multiple sensor units 110 may be used on a single user 105. The sensor units 110 may be worn or carried by the users 105 through any known means, for example as wearable chest straps or wristwatch-type devices, or the like. In other examples, the sensor units 110 may be integrated with the user's clothing. The data collected by the sensor units 110 may be wirelessly conveyed to either the local computing devices 115, 120 or to the remote computing device 145 (via the network 125 and server 135). Data transmission may occur via, for example, frequencies appropriate for a personal area network (such as Bluetooth or IR communications) or local or wide area network frequencies such as radio frequencies specified by the IEEE 802.15.4 standard.

Each data point recorded by the sensor units 110 may include an indication of the time the measurement was made (referred to herein as a "time stamp"). In some embodiments, the sensor units 110 are sensors configured to conduct periodic automatic measurements of one or more physiological or activity parameters. A user may wear or otherwise be attached to one or more sensor units 110 so that the sensor units 110 may measure, record, and/or report physiological data associated with the user.

The sensor units 110 may be discrete sensors, each having independent clocks. As a result, sensor units 110 may generate data with different frequencies. The data streams generated by the sensor units 110 may also be offset from each other. The sensor units 110 may each generate a data point at any suitable time interval.

The local computing devices 115, 120 may enable the user 105 and/or a local caregiver or coach to monitor the collected physiological and activity data. For example, the local computing devices 115, 120 may be operable to present data collected from sensor units 110 in a human-readable format. For example, the received data may be outputted as a display on a computer or a mobile device. The local computing devices 115, 120 may include a processor that may be operable to present data received from the sensor units 110 in a visual format. The local computing devices 115, 120 may also output data in an audible format using, for example, a speaker.

The local computing devices 115, 120 may be custom computing entities configured to interact with the sensor units 110. In some embodiments, the local computing devices 115, 120 and the sensor units 110 may be portions of a single sensing unit operable to sense and display physiological parameters, for example on a watch face. In another embodiment, the local computing devices 115, 120 may be general purpose computing entities such as a personal computing device, for example, a desktop computer, a laptop computer, a netbook, a tablet personal computer (PC), an iPod®, an iPad®, a smartphone (e.g., an iPhone®, an Android® phone, a Blackberry®, a Windows® phone, etc.), a mobile phone, a personal digital assistant (PDA), and/or any other suitable device operable to send and receive signals, store and retrieve data, and/or execute modules.

The local computing devices 115, 120 may include memory, a processor, an output, a data input and a communication module. The processor may be a general purpose processor, a Field Programmable Gate Array (FPGA), an Application Specific Integrated Circuit (ASIC), a Digital Signal Processor (DSP), and/or the like. The processor may be configured to retrieve data from and/or write data to the memory. The memory may be, for example, a random access memory (RAM), a memory buffer, a hard drive, a database, an erasable programmable read only memory (EPROM), an electrically erasable programmable read only memory (EEPROM), a read only memory (ROM), a flash memory, a hard disk, a floppy disk, cloud storage, and/or so forth. In some embodiments, the local computing devices 115, 120 may include one or more hardware-based modules (e.g., DSP, FPGA, ASIC) and/or software-based modules (e.g., a module of computer code stored at the memory and executed at the processor, a set of processor-readable instructions that may be stored at the memory and executed at the processor) associated with executing an application, such as, for example, receiving and displaying data from sensor units 110.

The data input module of the local computing devices 115, 120 may be used to manually input measured physiological and activity data instead of or in addition to receiving data from the sensor units 110. For example, a third-party user of the local computing device 115, 120 may make an observation as to one or more physiological or activity conditions of a user and record the observation using the data input module. A third-party user may be, for example, a nurse, a doctor, a coach, and/or any other medical healthcare or physical training professional authorized to record user observations; the user; and/or any other suitable user. For instance, the third-party user may measure the user's body temperature (e.g., using a stand-alone thermometer) and enter the measurement into the data input module. In some embodiments, the data input module may be operable to allow the third-party user to select "body temperature" and input the observed temperature into the data input module, e.g., using a keyboard. The data input module may time stamp the observation (or measurement) with the time the observation is input into the local computing devices 115, 120, or the local computing devices 115, 120 may prompt the third-party user to input the time the observation (or measurement) was made so that the time provided by the third-party user is used to time stamp the data point. In another example, a third-party user may observe that the user is upright, is walking, has been tackled, or the like, and may input corresponding activity observations into the local computing devices 115, 120.

The processor of the local computing devices 115, 120 may be operated to control operation of the output of the local computing devices 115, 120. The output may be a television, liquid crystal display (LCD) monitor, cathode ray tube (CRT) monitor, speaker, tactile output device, and/or the like. In some embodiments, the output may be an integral component of the local computing devices 115, 120. Similarly stated, the output may be directly coupled to the processor. For example, the output may be the integral display of a tablet and/or smartphone. In some embodiments, an output module may include, for example, a High Definition Multimedia Interface™ (HDMI) connector, a Video Graphics Array (VGA) connector, a Universal Serial Bus™ (USB) connector, a tip, ring, sleeve (TRS) connector, and/or any other suitable connector operable to couple the local computing devices 115, 120 to the output.

As described in additional detail herein, at least one of the sensor units 110 may be operable to transmit physiological and/or activity data to the local computing devices 115, 120 and/or to the remote computing device 145 continuously, at scheduled intervals, when requested, and/or when certain conditions are satisfied (e.g., during an alarm condition).

The remote computing device 145 may be a computing entity operable to enable a remote user to monitor the output of the sensor units 110. The remote computing device 145 may be functionally and/or structurally similar to the local computing devices 115, 120 and may be operable to receive data streams from and/or send signals to at least one of the sensor units 110 via the network 125. The network 125 may be the Internet, an intranet, a personal area network, a local area network (LAN), a wide area network (WAN), a virtual network, a telecommunications network implemented as a wired network and/or wireless network, etc. The remote computing device 145 may receive and/or send signals over the network 125 via communication links 150 and server 135.

The remote computing device 145 may be used by, for example, a healthcare professional or sports coach to monitor the output of the sensor units 110. In some embodiments, as described in further detail herein, the remote computing device 145 may receive an indication of physiological and/or activity data when the sensors detect an alert condition, when the healthcare provider or coach requests the information, at scheduled intervals, and/or at the request of the healthcare provider, coach, and/or the user 105. For example, the remote computing device 145 may be operable to receive summarized physiological and/or activity data from the server 135 and display the summarized data in a convenient format. The remote computing device 145 may be located, for example, at a nurses' station or in a user's room in some examples, or in other instances may be located at a personal computing device monitored by the coach or professional monitoring the user, and may be configured to display a summary of the physiological and/or activity data collected from one or more users. In some instances, the local computing devices 115, 120 may also be operable to receive and display physiological and/or activity data in much the same way that the remote computing device 145 is operable.

The server 135 may be configured to communicate with the sensor units 110, the local computing devices 115, 120, the third-party sensors 130, the remote computing device 145, and databases 140. The server 135 may perform additional processing on signals received from the sensor units 110, local computing devices 115, 120 or third-party sensors 130, or may simply forward the received information to the remote computing device 145 and databases 140. The databases 140 may be examples of electronic health records ("EHRs") and/or personal health records ("PHRs"), and may be provided by various service providers. The third-party sensor 130 may be a sensor that is not attached to the user 105 but that still provides data that may be useful in connection with the data provided by sensor units 110. In other examples, the third-party sensor 130 may be worn or carried by, or associated with, a third-party user, and data therefrom may be used for comparison purposes with data collected from the user 105. In certain embodiments, the server 135 may be combined with one or more of the local computing devices 115, 120 and/or the remote computing device 145.

The server 135 may be a computing device operable to receive data streams (e.g., from the sensor units 110 and/or the local computing devices 115, 120), store and/or process data, and/or transmit data and/or data summaries (e.g., to the remote computing device 145). For example, the server 135 may receive a stream of heart rate data from a sensor unit 110, a stream of oxygen saturation data from the same or a different sensor unit 110, and a stream of magnitude of force data from either the same or yet another sensor unit 110. In some embodiments, the server 135 may "pull" the data streams, e.g., by querying the sensor units 110 and/or the local computing devices 115, 120. In some embodiments, the data streams may be "pushed" from the sensor units 110 and/or the local computing devices 115, 120 to the server 135. For example, the sensor units 110 and/or the local computing devices 115, 120 may be configured to transmit data as it is generated by or entered into that device. In some instances, the sensor units 110 and/or the local computing devices 115, 120 may periodically transmit data (e.g., as a block of data or as one or more data points).

The server 135 may include a database (e.g., in memory) containing physiological and/or activity data received from the sensor units 110 and/or the local computing devices 115, 120. Additionally, as described in further detail herein, software (e.g., stored in memory) may be executed on a processor of the server 135. Such software (executed on the processor) may be operable to cause the server 135 to monitor, process, summarize, present, and/or send a signal associated with physiological data.

Although the server 135 and the remote computing device 145 are shown and described as separate computing devices, in some embodiments, the remote computing device 145 may perform the functions of the server 135 such that a separate server 135 may not be necessary. In such an embodiment, the remote computing device 145 may receive physiological and/or activity data streams from the sensor units 110 and/or the local computing devices 115, 120, process the received data, and display the processed data as summarized physiological and/or activity data.

Additionally, although the remote computing device 145 and the local computing devices 115, 120 are shown and described as separate computing devices, in some embodiments, the remote computing device 145 may perform the functions of the local computing devices 115, 120 such that a separate local computing device 115, 120 may not be necessary. In such an embodiment, the third-party user (e.g., a nurse or a coach) may manually enter the user's physiological data (e.g., the user's body temperature) directly into the remote computing device 145.

In one embodiment, network 125 may be a mesh network operated in accordance with the IEEE 802.15.4 standard, using, for example, TDM. Thus, for example, communication on the network 125 may be divided into discrete time intervals, with each time interval allowing for communications from or to individual devices. The server 135 may broadcast a beacon at a specific time interval, and the beacon may be received by individual sensor units 110. Individual sensor units 110 may use the beacon as a synchronization signal and then respond by sending collected physiological data to the server 135 at designated time slots.

Figure 2:
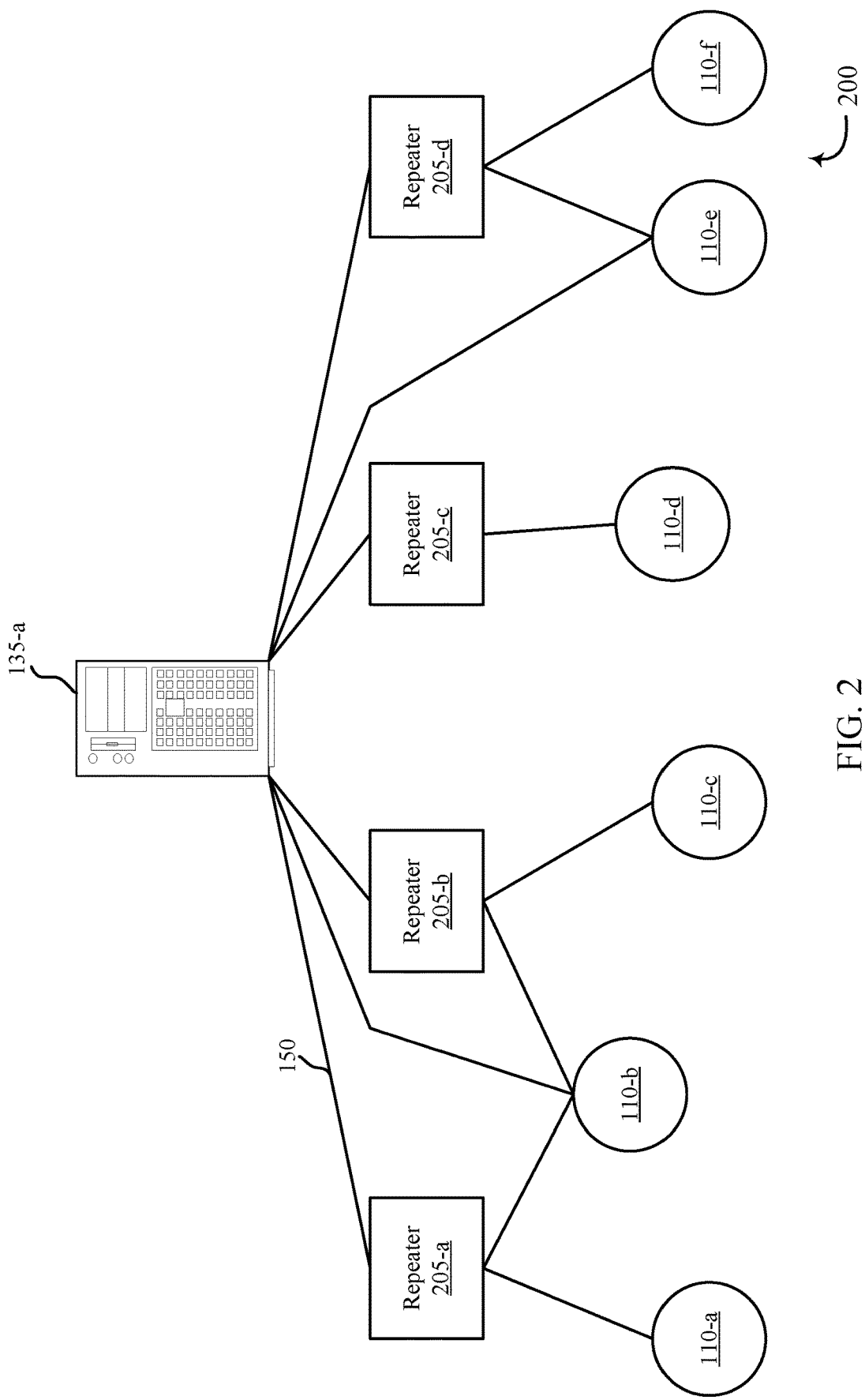
FIG. 2 is a block diagram of an example of a mesh network, in accordance with various embodiments.

FIG. 2 illustrates an example mesh network 200, in accordance with various aspects of the present disclosure. The mesh network 200 may be an example of the network 125 of FIG. 1, and may additionally include other components of the physiological and activity parameter monitoring system 100 of FIG. 1. For example, mesh network 200 may include a server 135-*a*, repeaters 205, and sensor units 110. In the example mesh network 200, four repeaters 205 are illustrated (repeaters 205-*a*, 205-*b*, 205-*c*, 205-*d*), and six sensor units 110 are illustrated (sensor units 110-*a*, 110-*b*, 110-*c*, 110-*d*, 110-*e*, 110-*f*). However, the numbers of repeaters 205 and/or sensor units 110 in the mesh network 200 may vary.

The sensor units 110, repeaters 205, and server 135-*a* may be in communication with each other via communication links 150. The illustrated communication links 150 are bi-directional and illustrate that sensor units 110 may be in communication with the server 135-*a* either directly or through one or more repeaters 205. Whether a communication link 150 is direct or via a repeater 205 may depend on proximity of the server 135-*a*, the repeaters 205, and the sensor units 110 to each other. For example, sensor unit 110-*a* may be within range of repeater 205-*a* but may not be in range of any other repeater 205 or the server 135-*a*. Repeater 205-*a*, however, may be in range of the server 135-*a*. Therefore, in this example, sensor unit 110-*a* may communicate with server 135-*a* via repeater 205-*a*. On the other hand, sensor unit 110-*b* may be within range of multiple repeaters (for example, repeaters 205-*a*, 205-*b*) and within range of the server 135-*a*. Therefore, sensor unit 110-*b* may communicate with server 135-*a* directly and/or via repeaters 205-*a*, 205-*b*.

When TDM is used in the mesh network 200, each device may be designated one or more time slots during which messages or data may be transmitted. Thus, and for example, the server 135-*a* may have a designated time during which the server 135-*a* may broadcast a beacon signal to be received by the sensor units 110. The broadcast beacon signal may be received directly by some sensor units 110, such as sensor unit 110-*b* or sensor unit 110-*e*. The broadcast beacon may also be received by each of the repeaters 205-*a*, 205-*b*, 205-*c*, 205-*d*. The repeaters 205-*a*, 205-*b*, 205-*c*, 205-*d* may each also have a designated time interval during which the repeaters 205 may each forward the received beacon to sensor units 110 that may be within range of respective repeaters 205. Thus, sensor unit 110-*c*, for example, may receive a broadcast beacon from repeater 205-*b* during a time interval designated for beacon retransmission by repeater 205-*b*. Sensor unit 110-*b*, for example, may receive a broadcast beacon from each of the server 135-*a*, repeater 205-*a*, and repeater 205-*b*. Thus, sensor unit 110-*b* may receive three copies of the beacon, each copy being received at a different time interval that corresponds to the transmitting entity.

Figure 3A:
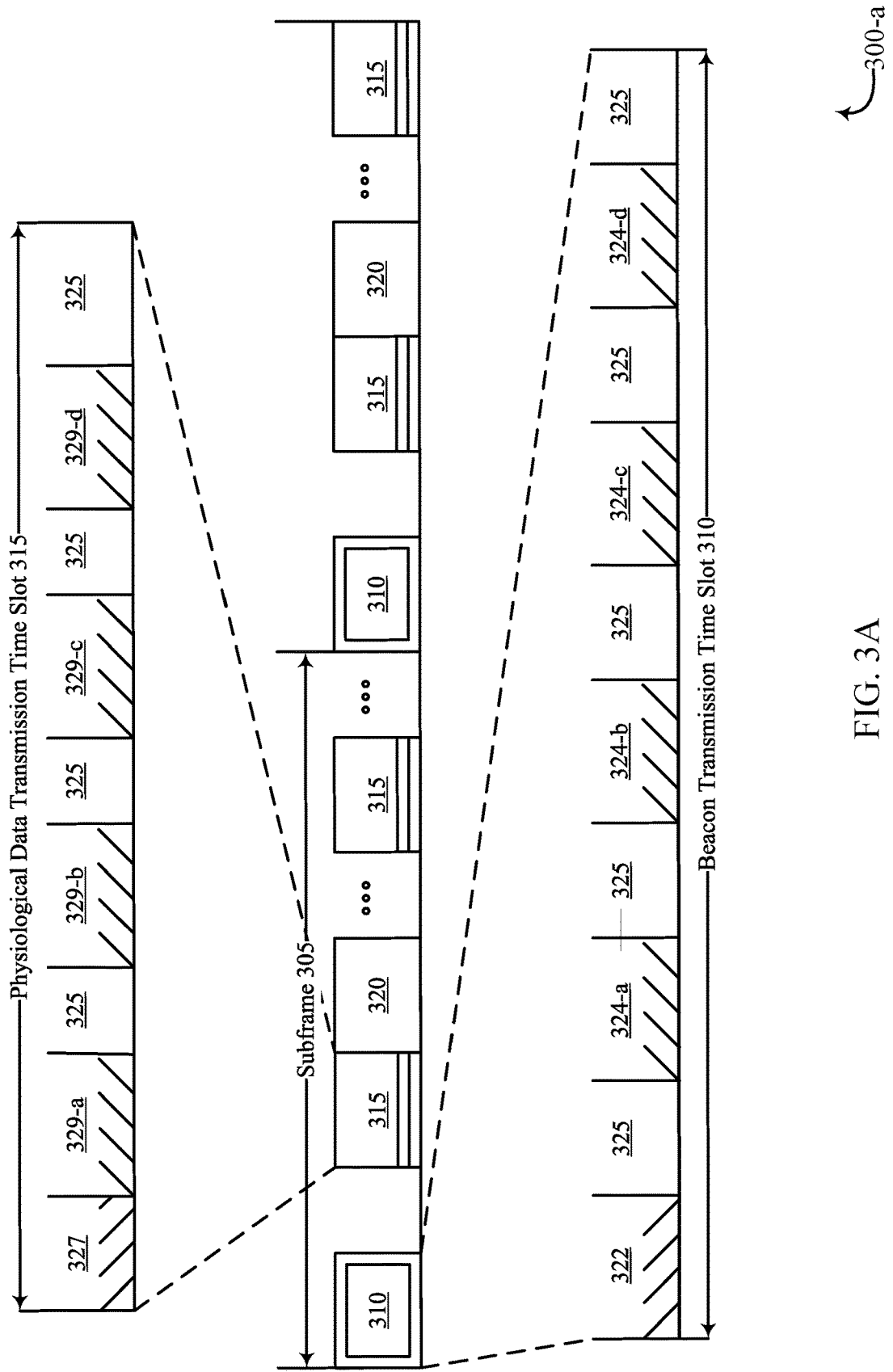
FIGS. 3A, 3B, and 3C are examples of transmission timelines and process flows for use in managing communication modes in a network, in accordance with various embodiments.
Figure 3B:
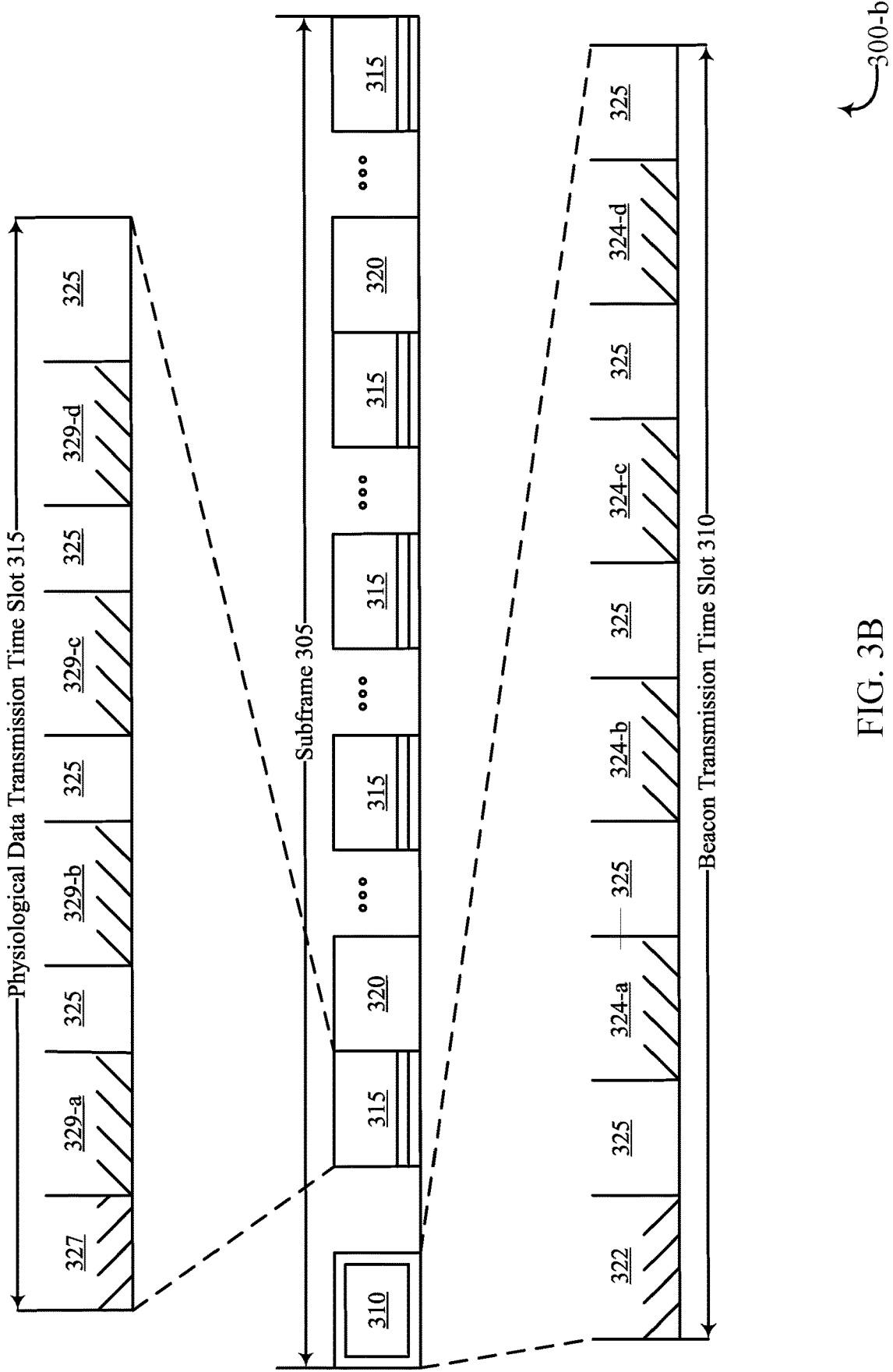
Figure 3C:
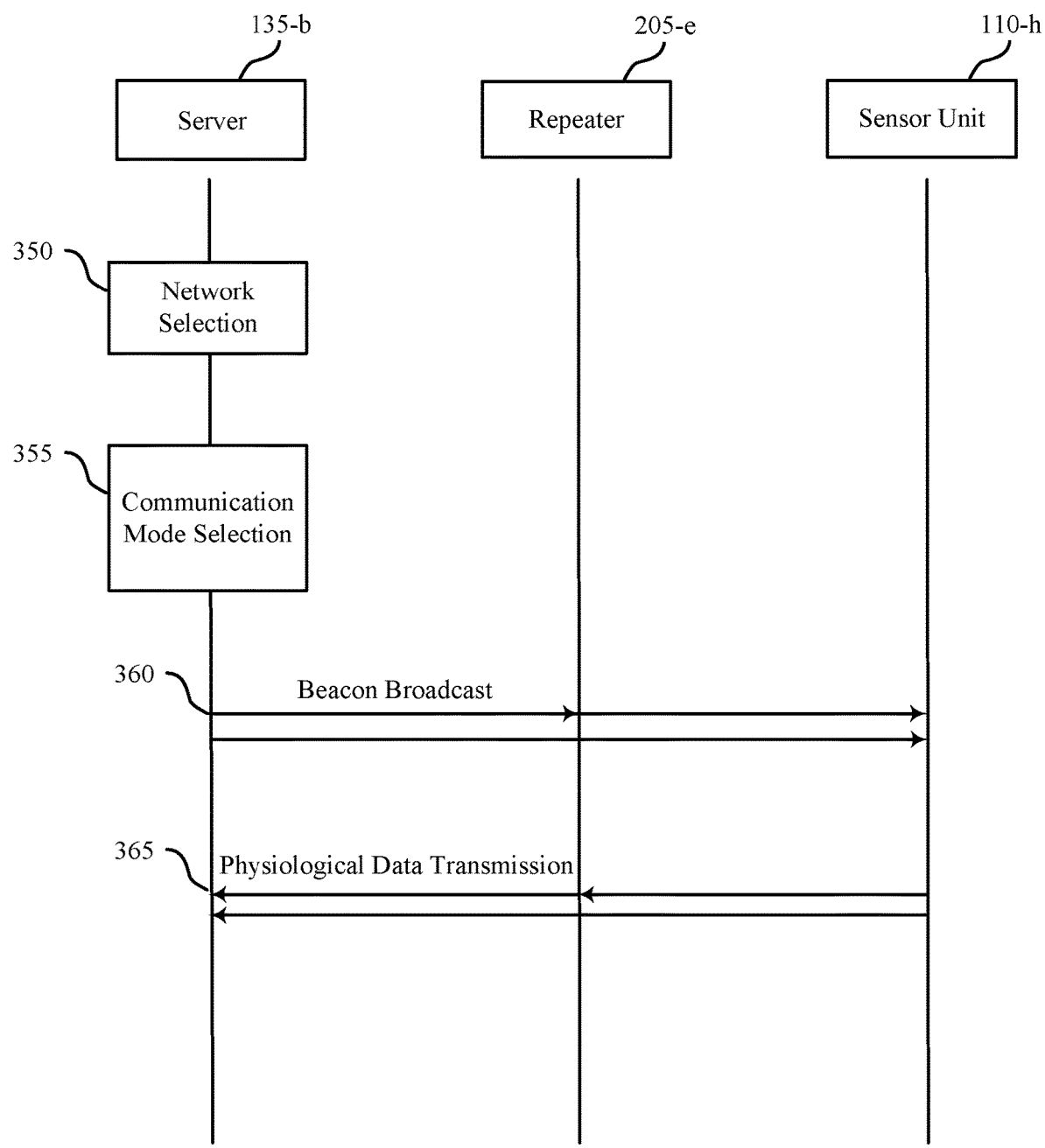

Similarly, sensor units 110 may also transmit data to the server 135-*a*. In the TDM system of mesh network 200, each sensor unit 110 may transmit collected physiological data, for example, during a time interval designated for transmission by the respective sensor unit 110. The transmitted data may be received at the server 135-*a* either directly or via a repeater 205. Repeaters 205 that receive data transmitted by a sensor unit 110 may retransmit the data during time intervals that are designated for repeater retransmission of data from specific sensor units 110. FIGS. 3A, 3B, and 3C illustrate the transmission timing in greater detail.

FIG. 3A illustrates an example transmission timeline 300-*a*, in accordance with various aspects of the present disclosure. The example transmission timeline 300-*a* may be used by the mesh network 200 of FIG. 2 to govern transmissions between sensor units 110 and the server 135 of FIGS. 1 and/or 2, for example. The transmission timeline 300-*a* may be divided into subframes 305. Each subframe 305 may be further subdivided into time slots 310, 315, 320, during which various types of transmissions are allowed to occur from various devices. For example, at the beginning of each subframe 305, time slot 310 may be reserved for beacon transmission. Each subframe 305 may further include time slots 315 that are reserved for transmission of physiological data from each sensor unit 110 within the mesh network 200. While example transmission timeline 300-*a* only illustrates two time slots 315 within each subframe 305, each subframe 305 may have a sufficient number of time slots 315 reserved so that each sensor unit 110 within mesh network 200 may be assigned a time slot 315. Additionally, one or more time slots 320 within each subframe 305 may be reserved for transmission of additional vital signs data from a sensor unit 110. The additional vital signs data may be transmitted in response to a request received from the server 135-*a* or to accompany an alert signal that may have been generated at the sensor unit 110 and transmitted during a corresponding time slot 315.

The beacon transmission time slot 310 may further be subdivided into time intervals for transmission of a beacon by the server 135-*a* and for retransmission of the beacon by repeaters 205. Thus, the beacon transmission time slot 310 may include an initial beacon transmission interval 322 as well as beacon retransmission intervals 324-*a*, 324-*b*, 324-*c*, 324-*d* (one for each repeater 205 that might receive the beacon). Guard time intervals 325 may be included between each transmission interval to reduce potential interference.

The physiological data transmission time slot 315 may also further be subdivided into time intervals for transmission of physiological data by a sensor unit 110 and for retransmission of the physiological data by repeaters 205. Thus, the physiological data transmission time slot 315 may include an initial physiological data transmission interval 327 as well as physiological data retransmission intervals 329-*a*, 329-*b*, 329-*c*, 329-*d* (one for each repeater 205 that might receive the physiological data transmission). Guard time intervals 325 may be included between each transmission interval to reduce potential interference.

Sensor units 110 may be assigned an address or identification that may be used to determine the specific time slot 315 to be used by each sensor unit 110. For example, a sensor unit 110 that is assigned a short address of 1 may be assigned to transmit on the first physiological data transmission time slot 315 of each subframe 305. A sensor unit 110 with short address 2 may be assigned to transmit on the second physiological data transmission time slot 315 of each subframe.

The actual timing of the example transmission timeline 300-*a* may vary based on the number of sensor units 110 within the mesh network 200. The actual timing may also be dependent upon a desired update rate for the received physiological data. Therefore, a crowded mesh network with a high update rate will result in transmission time intervals being shorter than those that might be used in a sparsely populated mesh network having a low update rate. Accordingly, the components of mesh network 200 may adjust their transmission timing based on a communicated number of devices within the network and a desired update rate. To simplify the transmission timing adjustment, specific communication modes may be used and communicated. Communication of a selected mode may be included within a beacon transmission, for example.

Sensor units 110 may be programmed to communicate using specific timing protocols that correspond to specific preset modes. For example, a sensor unit 110 may be configured to operate in one of at least three communication modes. A first mode may be a default mode that is configured for medium-sized networks and a default update rate. For example, a first mode may provide transmission time intervals for up to fifty sensor units 110 during each subframe 305 and may have an update rate (or subframe duration) of 2.5 seconds. This first mode could be referred to as a 2.5/50 mode, meaning that fifty devices may be on the network at any given time, each providing physiological data at 2.5-second rates. As another example, a second mode may be configured for small-sized networks having a faster update rate. For example, a second mode may provide transmission time intervals for up to twenty sensor units 110 during each subframe 305 and may have an update rate (or subframe duration) of one second. This second mode could be referred to as a 1/20 mode, meaning that twenty devices may be on the network at any given time, each providing physiological data at one-second rates. As a third example, a third mode may be configured for large-sized networks having a slower update rate. For example, a third mode may provide transmission time intervals for up to one hundred sensor units 110 during each subframe 305 and may have an update rate (or subframe duration) of five seconds. This third mode could be referred to as a 5/100 mode, meaning that one hundred devices may be on the network at any given time, each providing physiological data at five-second rates.

The specific mode being used may be selected by a user of the server 135-*a*. As explained above, the server 135-*a* may be a stand-alone component or may be integrated with one of the local computing devices 115, 120 or the remote computing device 145. Therefore, using software installed on the server 135-*a*, the local computing devices 115, 120, or the remote computing device 145, a user may both select a network to configure and a specific communication mode to be used on the selected network. A network identification and the selected communication mode may then be conveyed to the sensor units 110 via a beacon broadcast during the beacon transmission time slot 310. Upon receipt of a beacon that indicates that a communication mode has changed, a sensor unit 110 may adjust its transmission timing parameters to ensure that physiological data transmissions occur during the time intervals that correspond to the sensor unit 110 for the identified communication mode.

FIG. 3B illustrates an example transmission timeline 300-*b*, in accordance with various aspects of the present disclosure. The example transmission timeline 300-*b* may be used by the mesh network 200 of FIG. 2 to govern transmissions between sensor units 110 and the server 135 of FIGS. 1 and/or 2, for example. The transmission timeline 300-*b* is similar to that illustrated in FIG. 3A. However, example transmission timeline 300-*b* illustrates a timeline that could be used during, for example, the third communication mode described above, where the mesh network 200 includes a large number of sensor units 110. In the example transmission timeline 300-*b*, the subframe 305 is longer than that illustrated in FIG. 3A, reflecting that the update rate in the third communication mode may be much slower than that used in other communication modes. Example transmission timeline 300-*b* also illustrates that additional time has been incorporated into the subframe 305 to allow for multiple time slots 320 for transmission of additional vital signs data from a sensor unit 110. As additional vital signs data is generally only transmitted in response to a request or with an accompanying alert, a limited number of time slots 320 may be reserved for transmission of this additional vital signs data. However, as the number of sensor units 110 within a mesh network 200 increases (as in the third communication mode), a greater number of time slots 320 may be reserved for the on-demand or alert-based transmission of additional vital signs data.

FIG. 3C illustrates a process flow 300-*c* that corresponds to the transmission timelines 300-*a*, 300-*b* of FIGS. 3A and 3B, in accordance with various aspects of the present disclosure. In FIG. 3C, a server 135-*b*, a repeater 205-*e*, and a sensor unit 110-*h* are illustrated. The server 135-*b*, repeater 205-*e*, and sensor unit 110-*h* may be examples of the servers 135, repeaters 205, and sensor units 110 of FIGS. 1 and 2. As the server 135-*b* may also be integrated or in communication with the local computing devices 115, 120 or the remote computing device 145, the processes in FIG. 3C may also be considered as occurring at the local computing devices 115, 120 or the remote computing device 145.

At block 350, server 135-*b* may receive a network selection. A user may identify a network to be configured. The user may perform this identification at the local computing devices 115, 120 or the remote computing device 145, and the identification may then be received at the server 135-*b*. At block 355, server 135-*b* may receive a communication mode selection, as selected by a user. A user may select a communication mode to be applied to the selected network. The identified communication mode may correspond to a mode having a preselected maximum number of sensor units 110 in the network and a preselected update rate.

Once a network has been configured to function using a selected communication mode, the server 135-*b* may transmit a beacon broadcast 360 to the devices of the configured network. The beacon broadcast 360 may be received by a repeater 205-*e*, which may then retransmit the beacon broadcast 360 to a sensor unit 110-*h*. Alternatively, the beacon broadcast 360 may be received at the sensor unit 110-*h* directly from the server 135-*b*. The beacon may include an identification of the network and an identification of the selected communication mode.

Upon receipt of the beacon broadcast 360, the sensor unit 110-*h* may reconfigure its transmission protocols to conform to the timing corresponding to the communication mode identified in the received beacon broadcast 360. The sensor unit 110-*h* may then communicate with other entities in the network using the updated timing. For example, the sensor unit 110-*h* may send a sensor unit transmission 365 to the server 135-*b*. The sensor unit transmission 365 may be sent directly to the server 135-*b* or via the repeater 205-*e*. The sensor unit transmission 365 is sent using timing that corresponds to the identified communication mode timing.

Figure 4:
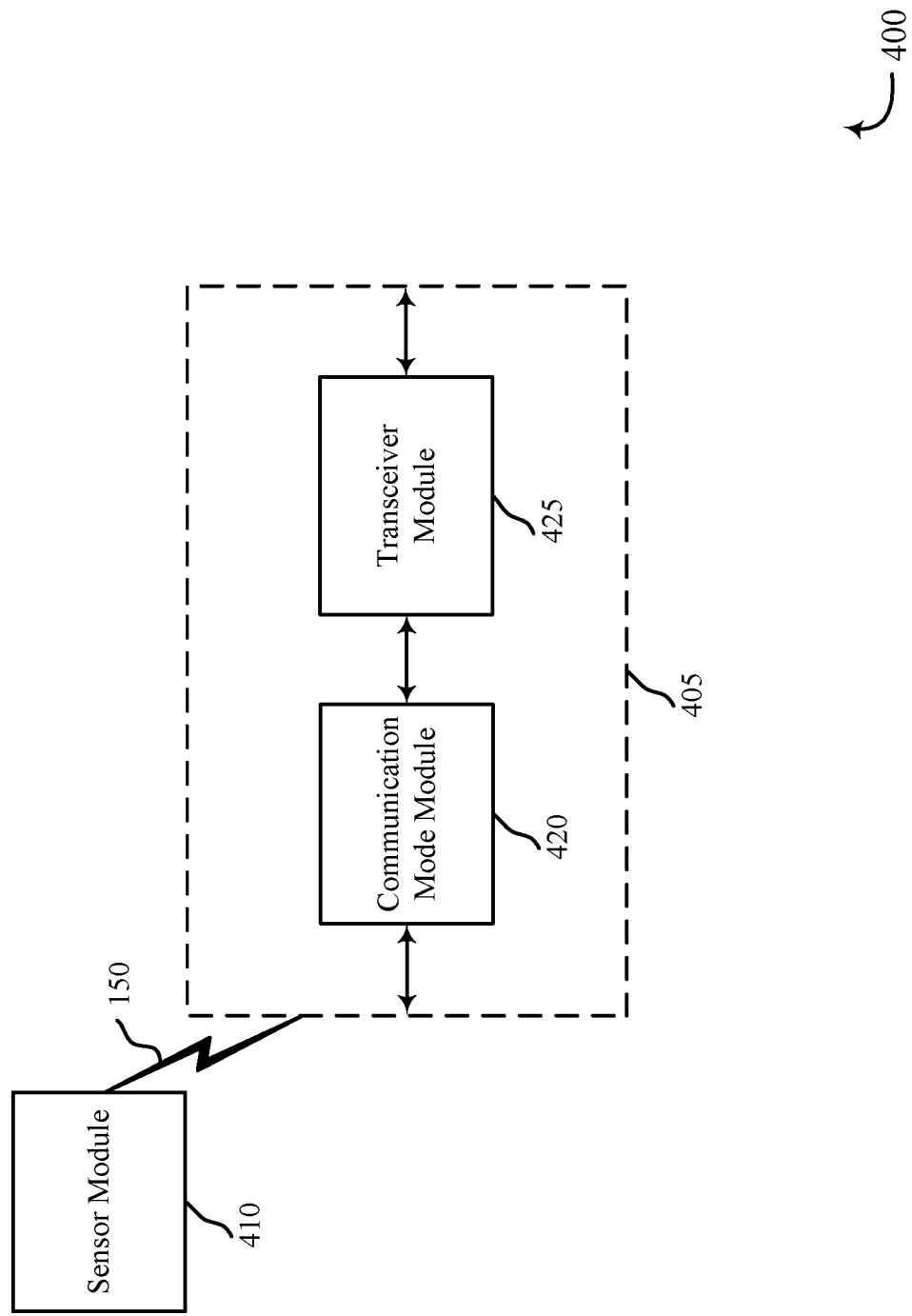
FIG. 4 is a block diagram of an example of an apparatus, in accordance with various embodiments.

FIG. 4 shows a block diagram 400 that includes apparatus 405, which may be an example of one or more aspects of the sensor unit 110, server 135, local computing devices 115, 120, and/or remote computing device 145 (of FIG. 1) for use in physiological and/or activity monitoring, in accordance with various aspects of the present disclosure. In some examples, the apparatus 405 may include a communication mode module 420 and a transceiver module 425. In some examples, one or more sensor modules 410 may be positioned externally to apparatus 405 and may communicate with apparatus 405 as sensor units 110 via wireless links 150, or in other examples the one or more sensor modules 410 may be components of apparatus 405. Each of these components may be in communication with each other.

The components of the apparatus 405 may, individually or collectively, be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used (e.g., Structured/Platform ASICs, Field Programmable Gate Arrays (FPGAs), and other Semi-Custom ICs), which may be programmed in any manner known in the art. The functions of each unit may also be implemented, in whole or in part, with instructions embodied in a memory, formatted to be executed by one or more general or application-specific processors.

In some examples, the transceiver module 425 may be operable to receive data streams from the sensor units 110 and/or sensor modules 210, as well as to send and/or receive other signals between the sensor units 110 and either the local computing devices 115, 120 or the remote computing device 145 via the network 125 and server 135. In an embodiment, the transceiver module 425 may receive data streams from the sensor units 110 and also forward the data streams to other devices. The transceiver module 425 may include wired and/or wireless connectors. For example, in some embodiments, sensor units 110 may be portions of a wired or wireless sensor network, and may communicate with the local computing devices 115, 120 and/or remote computing device 145 using either a wired or wireless network. The transceiver module 225 may be a wireless network interface controller ("NIC"), Bluetooth® controller, IR communication controller, ZigBee® controller and/or the like.

In some examples, the communication mode module 420 may include circuitry, logic, hardware and/or software for allowing a user to identify a network 125 and communication mode to be used with that network 125. The communication mode module 420 may include multiple modes and corresponding settings and/or parameters that may be implemented upon selection of a communication mode. If apparatus 405 is part of a server 135, for example, the communication mode module 420 may be configured to transmit as part of a beacon an indication of a selected mode. The communication mode module 420 may also ensure that the beacons are transmitted in accordance with the timing of the selected communication mode. If apparatus 405 is part of a sensor unit 110, for example, the communication mode module 420 may be configured to receive a beacon and extract from the beacon the identification of the selected communication mode. Upon identification of the communication mode, the communication mode module 420 may ensure that the apparatus 405 transmits messages in accordance with the received communication mode. Thus, the communication mode module 420 may adjust the timing of various transmissions to be sent by the sensor units 110 (via apparatus 405).

Figure 5:
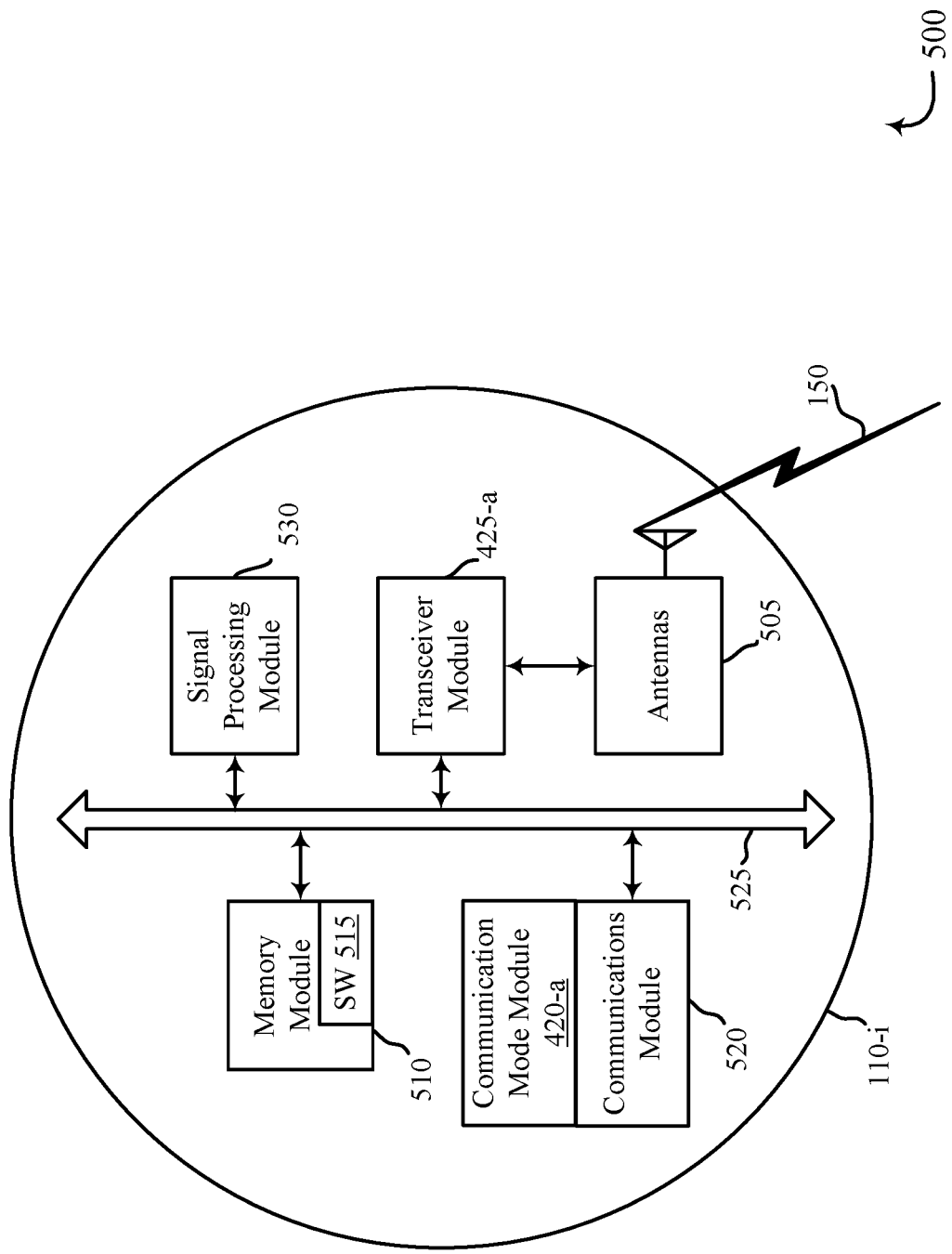
FIG. 5 is a block diagram of an example of an apparatus, in accordance with various embodiments.

FIG. 5 shows a block diagram 500 of a sensor unit 110-$i$ for use in remote physiological and activity monitoring, in accordance with various aspects of the present disclosure. The sensor unit 110-$i$ may have various configurations. The sensor unit 110-$i$ may, in some examples, have an internal power supply (not shown), such as a small battery, to facilitate mobile operation. In some examples, the sensor unit 110-$i$ may be an example of one or more aspects of one of the sensor units 110 and/or apparatus 405 described with reference to FIGS. 1-4. The sensor unit 110-$i$ may be configured to implement at least some of the features and functions described with reference to FIGS. 1-4.

The sensor unit 110-$i$ may include a signal processing module 530, a transceiver module 425-$a$, a communications module 520 that may be integrated with or include a communication mode module 420-$a$, at least one antenna (represented by antennas 505), or a memory module 510. Each of these components may be in communication with each other, directly or indirectly, over one or more buses 525. The communication mode module 420-$a$ and transceiver module 425-$a$ may be examples of the communication mode module 420 and transceiver module 425, respectively, of FIG. 4.

The memory module 510 may include RAM and/or ROM. The memory module 510 may store computer-readable, computer-executable code (SW) 515 containing instructions that are configured to, when executed, cause the communication mode module 420-$a$ to perform various functions described herein related to managing multiple communication modes on an identified network. Alternatively, the code 515 may not be directly executable by the communication mode module 420-$a$ but may be configured to cause the server 135 (of FIG. 1) (e.g., when compiled and executed) to perform various of the functions described herein.

The communication mode module 420-$a$ may include an intelligent hardware device, e.g., a CPU, a microcontroller, an ASIC, etc. The communication mode module 420-$a$ may process information received through the transceiver module 425-$a$ or information to be sent to the transceiver module 425-$a$ for transmission through the antenna 505. The communication mode module 420-$a$ may handle various aspects of managing transmission timing based on a received communication mode.

The transceiver module 425-$a$ may include a modem configured to modulate packets and provide the modulated packets to the antennas 505 for transmission, and to demodulate packets received from the antennas 505. The transceiver module 425-$a$ may, in some examples, be implemented as one or more transmitter modules and one or more separate receiver modules. The transceiver module 425-$a$ may support movement characterization communications. The transceiver module 425-$a$ may be configured to communicate bi-directionally, via the antennas 505 and communication link 150, with, for example, local computing devices 115, 120 and/or the remote computing device 145 (via network 125 and server 135 of FIG. 1). Communications through the transceiver module 425-$a$ may be coordinated, at least in part, by the communications module 520. While the sensor unit 110-$i$ may include a single antenna 505, there may be examples in which the sensor unit 110-$i$ may include multiple antennas 505.

Figure 6:
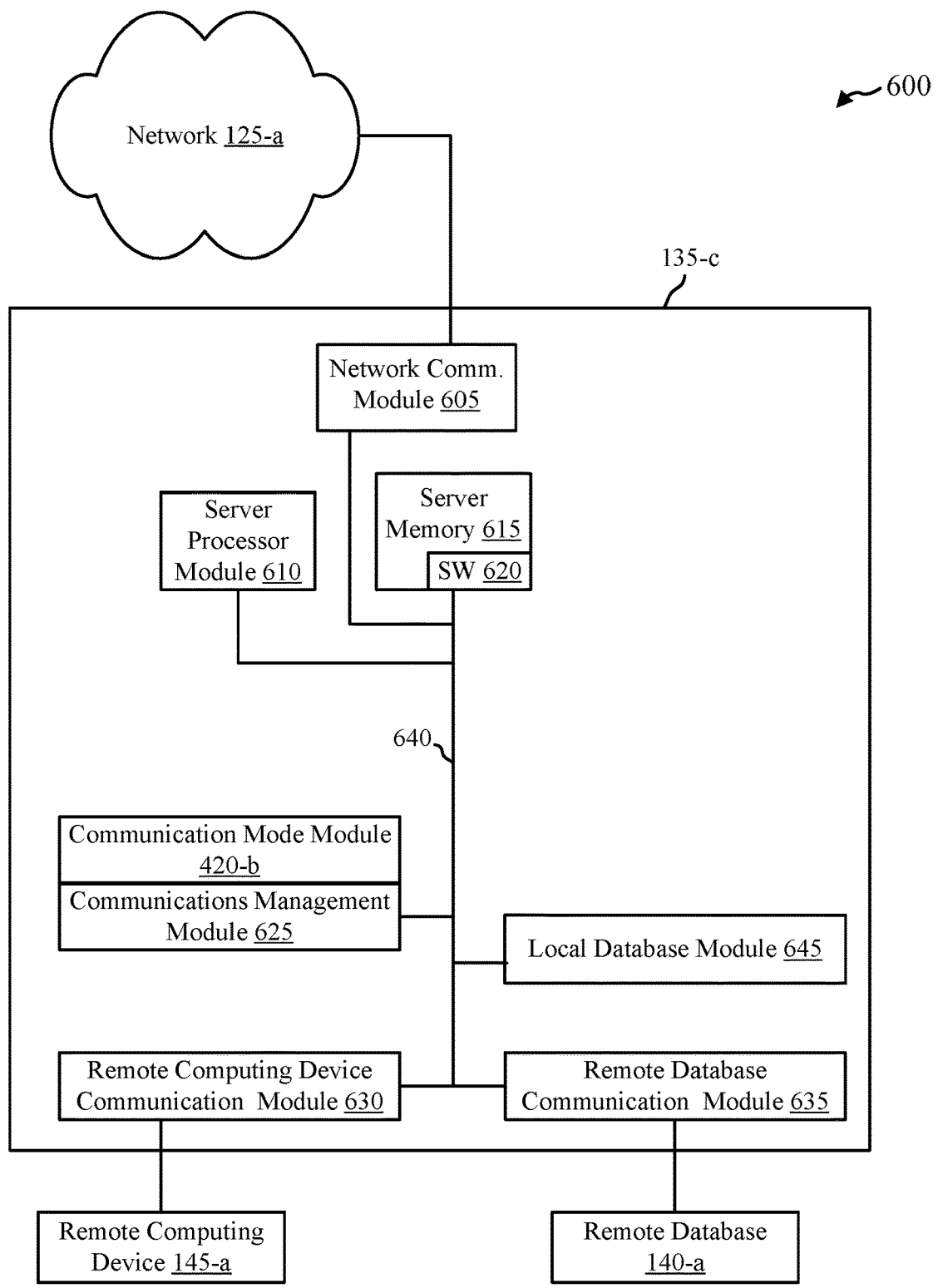
FIG. 6 is a block diagram of an example of a server for managing communication modes in a network, in accordance with various embodiments.

FIG. 6 shows a block diagram 600 of a server 135-c for use in remote physiological and activity monitoring, in accordance with various aspects of the present disclosure. In some examples, the server 135-c may be an example of aspects of the server 135 described with reference to FIGS. 1-4. In other examples, the server 135-c may be implemented in either the local computing devices 115, 120 or the remote computing device 145 of FIG. 1. The server 135-c may be configured to implement or facilitate at least some of the features and functions described with reference to the server 135, the local computing devices 115, 120 and/or the remote computing device 145 of FIGS. 1-4.

The server 135-c may include a server processor module 610, a server memory module 615, a local database module 645, and/or a communications management module 625, which may be integrated with or include a communication mode module 420-b. The server 135-c may also include one or more of a network communication module 605, a remote computing device communication module 630, and/or a remote database communication module 635. Each of these components may be in communication with each other, directly or indirectly, over one or more buses 640.

The server memory module 615 may include RAM and/or ROM. The server memory module 615 may store computer-readable, computer-executable code 620 containing instructions that are configured to, when executed, cause the server processor module 610 to perform various functions described herein related to managing communication modes. Alternatively, the code 620 may not be directly executable by the server processor module 610 but may be configured to cause the server 135-i (e.g., when compiled and executed) to perform various of the functions described herein.

The server processor module 610 may include an intelligent hardware device, e.g., a central processing unit (CPU), a microcontroller, an ASIC, etc. The server processor module 610 may process information received through the one or more communication modules 605, 630, 635. The server processor module 610 may also process information to be sent to the one or more communication modules 605, 630, 635 for transmission. Communications received at or transmitted from the network communication module 605 may be received from or transmitted to sensor units 110, local computing devices 115, 120, or third-party sensors 130 via network 125-a, which may be an example of the network 125 described in relation to FIGS. 1 and/or 2. Communications received at or transmitted from the remote computing device communication module 630 may be received from or transmitted to remote computing device 145-a, which may be an example of the remote computing device 145 described in relation to FIG. 1. Communications received at or transmitted from the remote database communication module 635 may be received from or transmitted to remote database 140-a, which may be an example of the remote database 140 described in relation to FIG. 1. Additionally, a local database may be accessed and stored at the server 135-c. The local database module 645 may be used to access and manage the local database, which may include data received from the sensor units 110, the local computing devices 115, 120, the remote computing devices 145 or the third-party sensors 130 (of FIG. 1).

The server 135-c may also include a communication mode module 420-b which may be configured to allow a user to identify a network and a communication mode to be used on that network. The communication mode module 420-b may also be used to configure a beacon with an identification of the selected network and communication mode. The communication mode module 420-b may be used to ensure that the server 135-c uses the appropriate timing for transmissions over network 125-a based on the selected communication mode.

Figure 7:
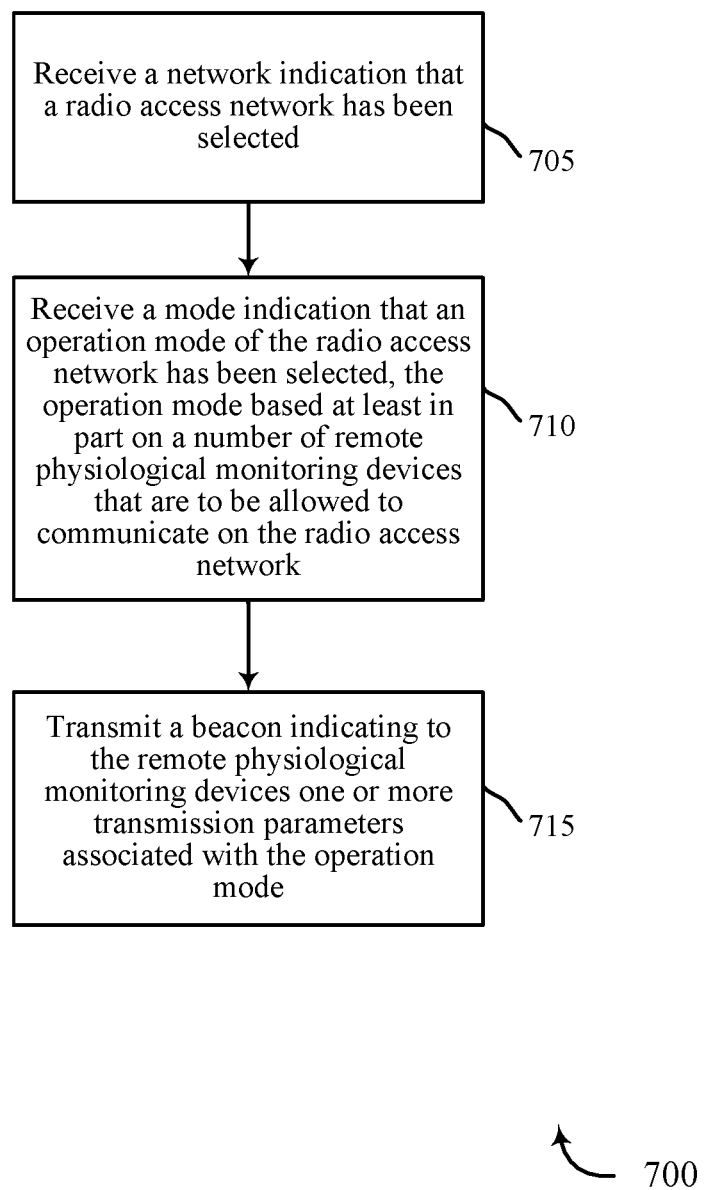
FIGS. 7 and 8 are flowcharts of various methods for managing communication modes in a network, in accordance with various embodiments.

FIG. 7 is a flow chart illustrating an example of a method 700 of wireless communication in a physiological status monitoring system, in accordance with various aspects of the present disclosure. For clarity, the method 700 is described below with reference to aspects of the server 135 or one or more of the local computing devices 115, 120, remote computing device 145 when integrated or in communication with the server 135 described with reference to FIGS. 1-4 and/or 6, or aspects of one or more of the apparatus 405 described with reference to FIG. 4. In some examples, a local computing device, remote computing device or server such as one of the local computing devices 115, 120, remote computing device 145, server 135 and/or an apparatus such as one of the apparatuses 405 may execute one or more sets of codes to control the functional elements of the local computing device, remote computing device, server, or apparatus to perform the functions described below.

At block 705, the method 700 may include receiving a network indication that a radio access network has been selected. The indication may reflect that a user has selected a network to be configured with a specific operating or communication mode.

At block 710, the method 700 may include receiving a mode indication that an operation mode of the radio access network has been selected. The operation or communication mode may be based at least in part on a number of remote physiological monitoring devices that are to be allowed to communicate on the radio access network. In certain aspects of the disclosure, the operation or communication mode may be based on a desired update rate. The sensor units 110 of FIG. 1 may be an example of the recited physiological monitoring devices.

At block 715, the method 700 may include transmitting a beacon indicating to the remote physiological monitoring devices one or more transmission parameters associated with the operation mode. The transmission parameters may include specific transmission timing requirements to be applied by the receiving remote physiological monitoring devices.

The operation or communication mode may correspond to a number of preset modes. For example, a first mode may be a default mode that is configured for medium-sized networks and a default update rate. For example, a first mode may provide transmission time intervals for up to fifty sensor units 110 during each subframe 305 and may have an update rate (or subframe duration) of 2.5 seconds. This first mode could be referred to as a 2.5/50 mode, meaning that fifty devices may be on the network at any given time, each providing physiological data at 2.5-second rates. As another example, a second mode may be configured for small-sized networks having a faster update rate. For example, a second mode may provide transmission time intervals for up to twenty sensor units 110 during each subframe 305 and may have an update rate (or subframe duration) of one second. This second mode could be referred to as a 1/20 mode, meaning that twenty devices may be on the network at any given time, each providing physiological data at one-second rates. As a third example, a third mode may be configured for large-sized networks having a slower update rate. For example, a third mode may provide transmission time intervals for up to one hundred sensor units 110 during each subframe 305 and may have an update rate (or subframe duration) of five seconds. This third mode could be referred to as a 5/100 mode, meaning that one hundred devices may be on the network at any given time, each providing physiological data at five-second rates.

In some embodiments, the operations at blocks 705, 710, or 715 may be performed using the communication mode module 420 described with reference to FIGS. 4 and/or 6. Nevertheless, it should be noted that the method 700 is just one implementation and that the operations of the method 700 may be rearranged or otherwise modified such that other implementations are possible.

Figure 8:
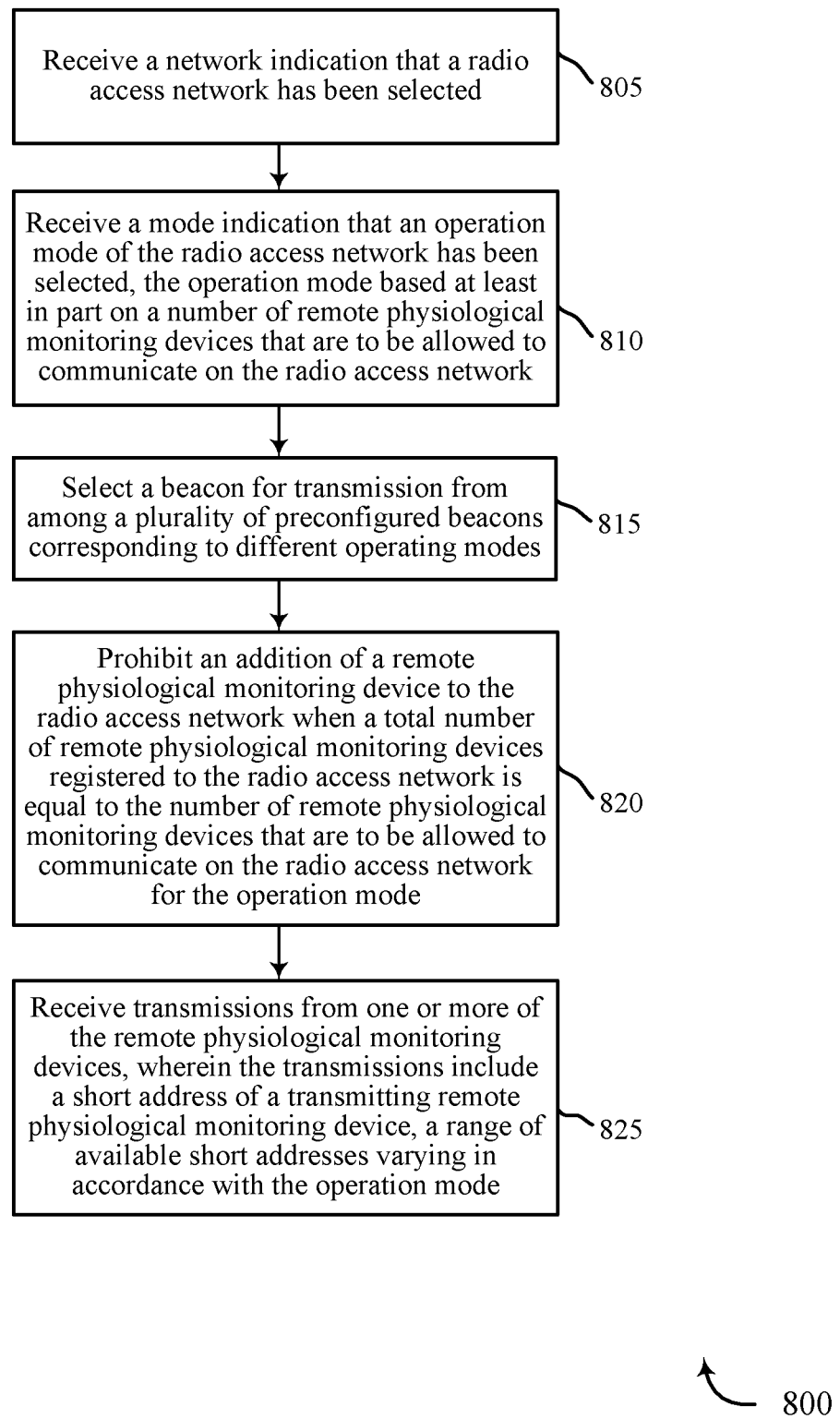

FIG. 8 is a flow chart illustrating an example of a method 800 of wireless communication in a physiological status monitoring system, in accordance with various aspects of the present disclosure. For clarity, the method 800 is described below with reference to aspects of the server 135 or one or more of the local computing devices 115, 120, remote computing device 145 when integrated or in communication with the server 135 described with reference to FIGS. 1-4 and/or 6, or aspects of one or more of the apparatus 405 described with reference to FIG. 4. In some examples, a local computing device, remote computing device or server such as one of the local computing devices 115, 120, remote computing device 145, server 135 and/or an apparatus such as one of the apparatuses 405 may execute one or more sets of codes to control the functional elements of the local computing device, remote computing device, server, or apparatus to perform the functions described below.

At block 805, the method 800 may include receiving a network indication that a radio access network has been selected. The indication may reflect that a user has selected a network to be configured with a specific operating or communication mode.

At block 810, the method 800 may include receiving a mode indication that an operation mode of the radio access network has been selected. The operation or communication mode may be based at least in part on a number of remote physiological monitoring devices that are to be allowed to communicate on the radio access network. In certain aspects of the disclosure, the operation or communication mode may be based on a desired update rate. The sensor units 110 of FIG. 1 may be an example of the recited physiological monitoring devices.

At block 815, the method 800 may include selecting a beacon for transmission from among a plurality of preconfigured beacons corresponding to different operating modes.

At block 820, the method 800 may include prohibiting an addition of a remote physiological monitoring device to the radio access network when a total number of remote physiological monitoring devices registered to the radio access network is equal to the number of remote physiological monitoring devices that are to be allowed to communicate on the radio access network for the operation mode. Thus, and for example, if a user selects an operation or communication mode for a network that is designed to allow a maximum of fifty sensor units to be in communication with the network at any given moment, then the communication mode module 420 (of FIGS. 4 and 6) may be configured to prevent any more than fifty sensor units to be added to the network.

At block 825, the method 800 may include receiving transmissions from one or more of the remote physiological monitoring devices, wherein the transmissions include a short address of a transmitting remote physiological monitoring device. The range of available short addresses may vary in accordance with the operation mode. Thus, and for example, if a user selects an operation or communication mode for a network that is designed to allow a maximum of fifty sensor units to be in communication with the network at any given moment, then the maximum number of short addresses available for this network will also be fifty.

In some embodiments, the operations at blocks 805, 810, 815, 820, or 825 may be performed using the communication mode module 420 described with reference to FIGS. 4 and/or 6. Nevertheless, it should be noted that the method 800 is just one implementation and that the operations of the method 800 may be rearranged or otherwise modified such that other implementations are possible.

The above description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, the methods described may be performed in an order different from that described, and various steps may be added, omitted, or combined. Also, features described with respect to certain embodiments may be combined in other embodiments.

The detailed description set forth above in connection with the appended drawings describes exemplary embodiments and does not represent the only embodiments that may be implemented or that are within the scope of the claims. The term "exemplary" used throughout this description means "serving as an example, instance, or illustration," and not "preferred" or "advantageous over other embodiments." The detailed description includes specific details for the purpose of providing an understanding of the described techniques. These techniques, however, may be practiced without these specific details. In some instances, well-known structures and devices are shown in block diagram form in order to avoid obscuring the concepts of the described embodiments.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, a FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration. A processor may in some cases be in electronic communication with a memory, where the memory stores instructions that are executable by the processor.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items indicates a disjunctive list such that, for example, a list of "at least one of A, B, or C" means A or B or C or AB or AC or BC or ABC (i.e., A and B and C).

A computer program product or computer-readable medium both include a computer-readable storage medium and communication medium, including any mediums that facilitates transfer of a computer program from one place to another. A storage medium may be any medium that may be accessed by a general purpose or special purpose computer. By way of example, and not limitation, computer-readable medium may comprise RAM, ROM, EEPROM, CD-ROM or other optical disk storage, magnetic disk storage or other magnetic storage devices, or any other medium that may be used to carry or store desired computer-readable program code in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote light source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and blu-ray disc where disks usually reproduce data magnetically, while discs reproduce data optically with lasers. Combinations of the above are also included within the scope of computer-readable media.

The previous description of the disclosure is provided to enable a user skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

The invention claimed is:

1. A method of wireless communication in a physiological status monitoring system, comprising:
   receiving a network indication that a radio access network has been selected from a plurality of radio access networks;
   receiving a mode indication that an operation mode for the radio access network has been selected for a timing of communications of each remote physiological monitoring device in the radio access network, the operation mode based at least in part on a number of remote physiological monitoring devices that are to be allowed to communicate on the radio access network;
   transmitting, to the remote physiological monitoring devices, a beacon indicating to the remote physiological monitoring devices one or more transmission parameters associated with the operation mode; and
   receiving transmissions from one or more of the remote physiological monitoring devices, wherein the transmissions include a short address of a transmitting remote physiological monitoring device, wherein the short address is within a range of available short addresses varying in accordance with the operation mode.

2. The method of claim 1, further comprising:
receiving transmissions from one or more of the remote physiological monitoring devices in accordance with the one or more transmission parameters.

3. The method of claim 1, further comprising:
selecting the beacon for transmission from among a plurality of preconfigured beacons corresponding to different operating modes.

4. The method of claim 1, further comprising:
receiving transmissions from one or more of the remote physiological monitoring devices at varying update rates, the update rates varying based on the operation mode.

5. The method of claim 1, further comprising:
operating in one of a low capacity operation mode, a medium capacity operation mode, or a high capacity operation mode, wherein the one or more transmission parameters indicate that the remote physiological monitoring devices are to provide updated data at a first update rate during operation in the low capacity operation mode, at a second update rate during operation in the medium capacity operation mode, and at a third update rate during operation in the high capacity operation mode.

6. The method of claim 5, wherein the first update rate has an update frequency that is faster than an update frequency of the second update rate, and wherein the second update rate has an update frequency that is faster than an update frequency of the third update rate.

7. The method of claim 1, wherein transmitting the beacon indicating to the remote physiological monitoring devices one or more transmission parameters associated with the operation mode comprises:
including in one or more transmission parameters an indication that the remote physiological monitoring devices are to provide updated data during transmission slots whose lengths vary in accordance with the operating mode.

8. The method of claim 1, wherein transmitting the beacon indicating to the remote physiological monitoring devices one or more transmission parameters associated with the operation mode comprises:
including the network indicator in the beacon.

9. The method of claim 1, further comprising:
prohibiting an addition of a remote physiological monitoring device to the radio access network when a total number of remote physiological monitoring devices registered to the radio access network is equal to the number of remote physiological monitoring devices that are to be allowed to communicate on the radio access network for the operation mode.

10. A physiological status monitoring device, comprising:
a transceiver configured to transmit and receive communications from one or more remote physiological monitoring devices; and a processor configured to execute instructions to:
- receive a network indication that a radio access network has been selected from a plurality of radio access networks;
- receive a mode indication that an operation mode for the radio access network has been selected for a timing of communications of each remote physiological monitoring device in the radio access network, the operation mode based at least in part on a number of remote physiological monitoring devices that are to be allowed to communicate on the radio access network;
- transmit, to the remote physiological monitoring devices, a beacon indicating to the remote physiological monitoring devices one or more transmission parameters associated with the operation mode; and
- receive transmissions from one or more of the remote physiological monitoring devices, wherein the transmissions include a short address of a transmitting remote physiological monitoring device, wherein the short address is within a range of available short addresses varying in accordance with the operation mode.

11. The device of claim 10, the processor being further configured to execute instructions to:
receive transmissions from one or more of the remote physiological monitoring devices in accordance with the one or more transmission parameters.

12. The device of claim 10, the processor being further configured to execute instructions to:
select the beacon for transmission from among a plurality of preconfigured beacons corresponding to different operating modes.

13. The device of claim 10, the processor being further configured to execute instructions to:
receive transmissions from one or more of the remote physiological monitoring devices at varying update rates, the update rates varying based on the operation mode.

14. The device of claim 10, the processor being further configured to execute instructions to:
operate in one of a low capacity operation mode, a medium capacity operation mode, or a high capacity operation mode, wherein the one or more transmission parameters indicate that the remote physiological monitoring devices are to provide updated data at a first update rate during operation in the low capacity operation mode, at a second update rate during operation in the medium capacity operation mode, and at a third update rate during operation in the high capacity operation mode.

15. The device of claim 10, wherein the instructions to transmit the beacon indicating to the remote physiological monitoring devices one or more transmission parameters associated with the operation mode comprise instructions executable on the processor to:
include in one or more transmission parameters an indication that the remote physiological monitoring devices are to provide updated data during transmission slots whose lengths vary in accordance with the operating mode.

16. The device of claim 10, wherein the instructions to transmit the beacon indicating to the remote physiological monitoring devices one or more transmission parameters associated with the operation mode comprise instructions executable on the processor to:
include the network indicator in the beacon.

17. The device of claim 10, the processor being further configured to execute instructions to:
prohibit an addition of a remote physiological monitoring device to the radio access network when a total number of remote physiological monitoring devices registered to the radio access network is equal to the number of remote physiological monitoring devices that are to be allowed to communicate on the radio access network for the operation mode.

18. A non-transitory computer-readable medium storing computer-executable code, the code executable by a processor to:
- receive a network indication that a radio access network has been selected from a plurality of radio access networks;
- receive a mode indication that an operation mode for the radio access network has been selected for a timing of communications of each remote physiological monitoring device in the radio access network, the operation mode based at least in part on a number of remote physiological monitoring devices that are to be allowed to communicate on the radio access network;
- transmit, to the remote physiological monitoring devices, a beacon indicating to the remote physiological monitoring devices one or more transmission parameters associated with the operation mode; and
- receive transmissions from one or more of the remote physiological monitoring devices, wherein the transmissions include a short address of a transmitting remote physiological monitoring device, wherein the short address is within a range of available short addresses varying in accordance with the operation mode.

* * * * *